(12) United States Patent
Sakaguchi et al.

(10) Patent No.: US 6,417,415 B1
(45) Date of Patent: Jul. 9, 2002

(54) METHODS OF SOLIDIFYING LOW-BOILING-POINT HYDROCARBON AND HANDLING THE SAME, AND REGENERATION THEREOF

(75) Inventors: Hiroshi Sakaguchi, Tsukuba; Tomokazu Yoshimura, Kumamoto, both of (JP); Rumiana Tzoneva, Sofia (BG); Takashi Masuda, Tsukuba (JP); Takahiro Sato, Tsukuba (JP); Akio Matsuda, Tsukuba (JP)

(73) Assignee: Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/539,717

(22) Filed: Mar. 31, 2000

(30) Foreign Application Priority Data

Aug. 10, 1999 (JP) ......................... 1999-226302
Aug. 30, 1999 (JP) ......................... 1999-242848

(51) Int. Cl.[7] .............. C07C 7/20; C07C 9/10; C07C 9/12; C07C 11/06; C07C 11/08; C07B 63/04
(52) U.S. Cl. ................ 585/3; 585/2; 585/801; 585/855; 585/864; 585/899; 585/932; 252/184
(58) Field of Search .................. 252/184, 372, 252/363.5, 183.11, 183.12; 585/2, 6, 3, 16, 801, 820, 830, 833, 839, 855, 864, 899, 932, 930

(56) References Cited

FOREIGN PATENT DOCUMENTS

| JP | 55075493 | 6/1980 | |
|----|----------|--------|---|
| JP | 56-157492 | 12/1981 | |
| JP | 59142274 | 8/1984 | |
| JP | 62-265393 | 11/1987 | |
| JP | 1-174595 | * | 7/1989 |
| JP | 1-201394 | * | 8/1989 |

* cited by examiner

Primary Examiner—Joseph D. Anthony
(74) Attorney, Agent, or Firm—Birch, Stewart, Kolasch & Birch, LLP

(57) ABSTRACT

Disclosed are a method of solidifying a low-boiling-point hydrocarbon, wherein the low-boiling-point hydrocarbon (including hydrocarbons which are gaseous at ordinary temperature) is brought into contact with a metal salt of an aliphatic carboxylic acid, and if necessary a high-boiling-point hydrocarbon, suspended in water, to form a solid aggregate substance, a method of handling the low-boiling-point hydrocarbon, wherein the solid aggregate substance is stored or transported, and a method of regenerating the low-boiling-point hydrocarbon, wherein the solid aggregate substance is decomposed by opening or heating, to obtain the low-boiling-point hydrocarbon. According to the methods, a wide variety of gaseous and highly volatile liquid hydrocarbons can be safely and easily solidified without using harmful reagent, and during storage, transportation, etc., the gaseous hydrocarbons and highly volatile liquids can be handled as a solid material. Further, by releasing under atmospheric pressure at room temperature or by heating if necessary, the original hydrocarbons can be easily obtained.

7 Claims, 2 Drawing Sheets

METHODS OF SOLIDIFYING LOW-BOILING-POINT HYDROCARBON AND HANDLING THE SAME, AND REGENERATION THEREOF

FIELD OF THE INVENTION

The present invention relates to a method of solidifying low-boiling-point hydrocarbons (e.g., hydrocarbons that are liquid with a high vapor pressure at ordinary temperature, as well as hydrocarbons that are gaseous at ordinary temperature), a method of regenerating this solidified product into low-boiling-point hydrocarbons in the original state, and a method of handling low-boiling-point hydrocarbons by utilizing these methods.

BACKGROUND OF THE INVENTION

As the scale of the petrochemical industry is enlarging year by year, organic compounds are produced and consumed in a large amount, and further, natural gas is used in a large amount. In this connection, pollution and accidents threatening the existence of mankind and living creatures, such as environmental pollution, water pollution, pollution of the ocean by tanker accidents; fires, and explosion accidents, occur frequently and worldwide, and the handling of organic compounds, including petrochemical materials, is an important issue. One cause for such pollution and accidents is mistakes made by people or inadequate safety measures, such as incomplete combustion, leakage, and release. Another and essential cause is, as a matter of course, that many of the organic compounds that have caused pollution and accidents are highly volatile liquids or gases. In particular, a basic requirement in the petroleum chemistry and the natural gas chemical industry is that gaseous organic substances can be handled safely at ordinary temperature.

In addition, the method of handling organic compounds used as industrial raw materials during storage and transportation, as well as costs thereof, is greatly influenced by the gaseous state of most such organic compounds. This is a fundamental problem in modern petrochemistry, including utilization of natural gas, and this is not an issue that can be solved by switching to carbochemistry or to utilization of solid fuels, such as charcoal.

As to this problem, it is proposed that gaseous organic compounds should be handled in a safer state during storage, transportation, etc. Attempts at this include handling an organic gas, such as methane, as a stable hydrate, i.e. methane hydrate (generally gas hydrate), by inclusion thereof into a cage structure formed by hydrogen bonds of water molecules, but it cannot be said that this attempt has been completed as practically usable techniques. Further, methane hydrate (gas hydrate) essentially requires several times or more water molecules than organic gases, and thus a very large amount of unnecessary water must be handled simultaneously.

In the case of hydrogen, for example, a hydrogen-occlusion alloy, which can reversibly occlude and release a hydrogen gas repeatedly, has been proposed, but for organic compounds, no such substance capable of reversible occlusion and release has been found.

Accordingly, it is desired that low-boiling-point liquid hydrocarbons and gaseous hydrocarbons can be handled as safe solids during storage, transportation, etc., while the original hydrocarbons can be taken out from the solid when used. It is considered that the requirements for such solidified materials of hydrocarbons are, for example, that they must be (1) repeatedly usable, (2) chemically relatively stable, and (3) safe and harmless, because their use in a large amount is estimated, and they are less dangerous even if they are discharged to the outside of the storage system.

Proposed methods of solidifying organic compounds that are liquid at ordinary temperature are described in JP-A-55-75493 ("JP-A" means unexamined published Japanese patent application) and JP-A-59-142274, but these methods involve utilizing hydrophilic groups in the compounds, thereby incorporating water and solidifying the compounds. Further, there is no description therein of a method of solidifying hydrocarbons that are gaseous or highly volatile liquid at ordinary temperature, and the solids described in these literatures cannot be reused when necessary by decomposition, to take out only hydrocarbons therefrom.

SUMMARY OF THE INVENTION

Accordingly, an object of the present invention is to provide a method of realizing reversible solidification of low-boiling-point hydrocarbons (including hydrocarbons that are gaseous at ordinary temperature) by utilizing materials satisfying the conditions as described above; that is, an object of the present invention is to provide a method of solidifying low-boiling-point hydrocarbons, a method of taking out low-boiling-point hydrocarbons in the original state from the solidified product, and a method of handling low-boiling-point hydrocarbons by using these methods.

Other and further objects, features, and advantages of the invention will appear more fully from the following description, taken in connection with the accompanying drawings.

DETAILED DESCRIPTION OF THE INVENTION

Figure 1:
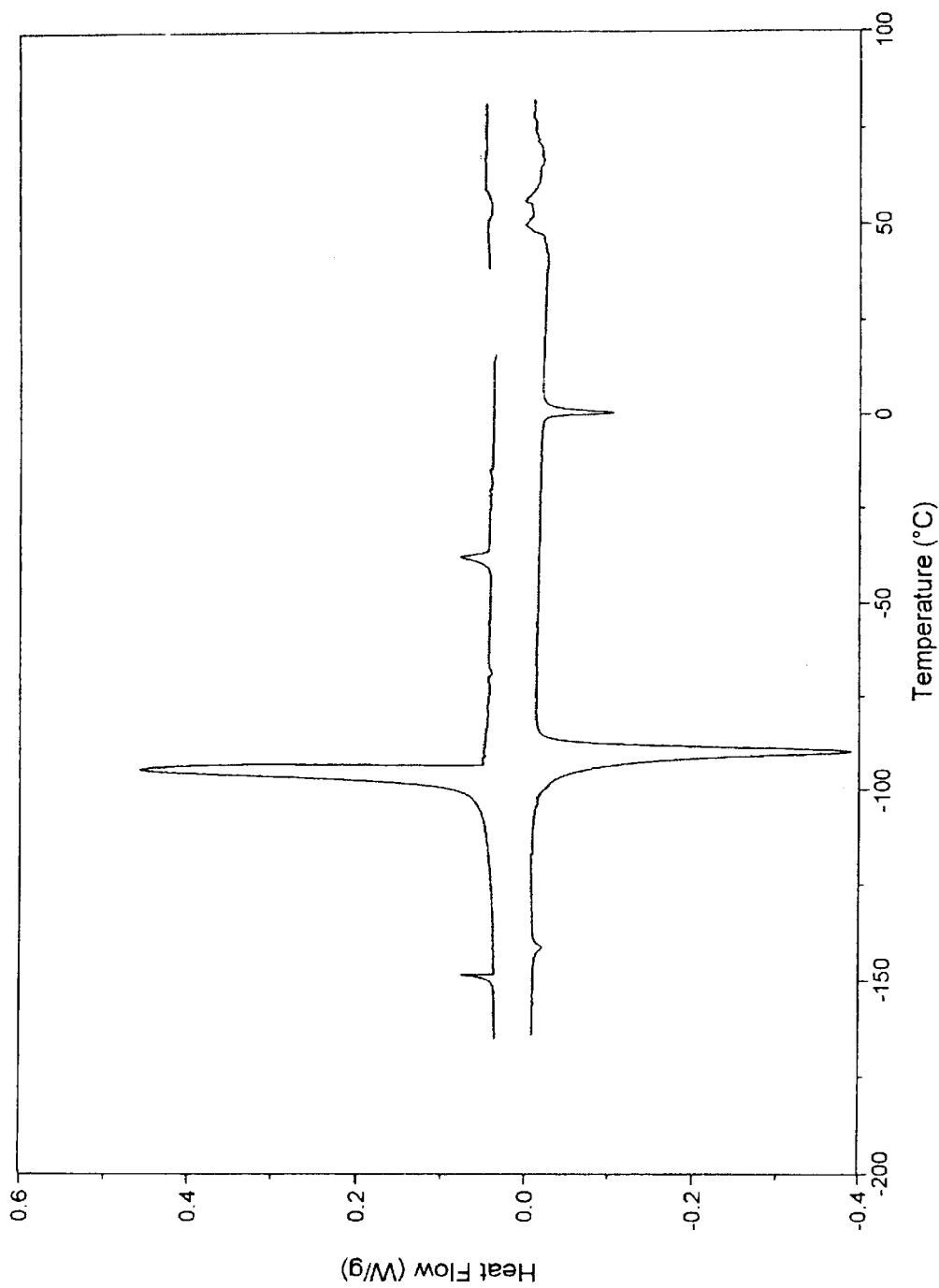
FIG. 1 is a graph showing the result of differential scanning calorimetry (DSC) of the white waxy solid aggregate substance in Example 1. Exothermal peaks in a cooling step are shown above, and endothermic peaks in a heating step are shown below.

The present inventors studied the interaction based on van der Waals force in water between n-paraffins and a surfactant having a long-chain alkyl group, and found that the surfactant can easily form a macroscopic aggregate substance with short-chain n-paraffins, and also fix low-boiling-point and low-melting-point n-paraffins, to solidify them. Further, we found that other hydrocarbons can also be solidified. After extensive studies based on this finding, the present invention was made.

That is, the present invention provides:

(1) A method of solidifying a low-boiling-point hydrocarbon, wherein the low-boiling-point hydrocarbon is brought into contact with a metal salt of an aliphatic carboxylic acid and a high-boiling-point hydrocarbon suspended in water, to form a solid aggregate substance (referred to hereinafter as the first aspect of the invention);

(2) A method of handling a low-boiling-point hydrocarbon, wherein the solid aggregate substance obtained by the solidification method described in the above (1) is stored or transported (referred to hereinafter as the second aspect of the invention);

(3) A method of regenerating a low-boiling-point hydrocarbon, wherein the solid aggregate substance obtained by the solidification method described in the above (1) is decomposed by heating, to obtain the low-boiling-point hydrocarbon (referred to hereinafter as the third aspect of the invention);

(4) A method of solidifying a gaseous hydrocarbon, wherein a metal salt of an aliphatic carboxylic acid, and a hydrocarbon that is a gas at ordinary temperature, are dissolved, emulsified, or suspended in water, to form a solid aggregate substance of the hydrocarbon (referred to hereinafter as the fourth aspect of the invention);

(5) A method of handling a gaseous hydrocarbon, wherein the solid aggregate substance obtained by the solidification method described in the above (4) is stored or transported (referred to hereinafter as the fifth aspect of the invention); and (6) A method of regenerating a gaseous hydrocarbon, wherein the solid aggregate substance obtained by the solidification method described in the above (4) is decomposed by opening or heating, to obtain the gaseous hydrocarbon (referred to hereinafter as the sixth aspect of the invention).

In the first to third aspects of the invention described above, the low-boiling-point hydrocarbons forming a solid aggregate substance mean hydrocarbons which are gaseous or liquid having a high vapor pressure at ordinary temperature (20° C.). The high-boiling-point hydrocarbons and low-boiling-point hydrocarbons are compounds composed of carbon atoms and hydrogen atoms, and they are preferably free from oxygen atoms, nitrogen atoms, sulfur atoms, etc. The solid aggregate substance in the first to third aspects of the invention is formed in water from a metal salt of an aliphatic carboxylic acid and the hydrocarbon described above, and the formed aggregate substance does not contain water. The solid aggregate substance formed in the first aspect of the invention is maintained stably in a solid state, in a closed vessel generally at room temperature (preferably 10 to 35° C., more preferably 20 to 25° C.) or less, preferably at room temperature or less, and low-boiling-point hydrocarbon can be taken out from the aggregate substance upon decomposition by heating preferably at 70° C. or more.

In the fourth to sixth aspects of the invention described above, the gaseous hydrocarbons forming a solid aggregate substance mean compounds composed of carbon atoms and hydrogen atoms, which are gaseous at ordinary temperature (20° C.), and these compounds are preferably free from oxygen atoms, nitrogen atoms, sulfur atoms, etc. The solid aggregate substance of the gaseous hydrocarbon in the fourth to sixth aspects of the invention is a white and gel-like or rice cake-like macroscopic aggregate substance consisting of a metal salt of an aliphatic carboxylic acid and a hydrocarbon, which is a molecular aggregate substance aggregated due to the van der Waals force between alkyl chains of the metal salt of an aliphatic carboxylic acid and the hydrocarbon. This aggregate substance is maintained stably in a solid state, in a closed vessel generally at room temperature or less, from which the original gaseous hydrocarbon can be taken out by opening the closed vessel or by heating the aggregate substance in the closed vessel.

The metal salt of an aliphatic carboxilic acid used in the present invention (referred to hereinafter as a metal salt of a carboxylic acid) is not particularly limited, and it is a metal salt of a carboxylic acid that is preferably straight-chain or branched or that has unsaturated bond(s) in the middle of a carbon chain. The number of carbon atoms in the metal salt of a carboxylic acid is preferably 4 to 22, particularly preferably 11 to 18, in the first to third aspects of the invention, or preferably 9 to 20, more preferably 12 to 18, in the fourth to sixth aspects of the invention. The type of the metal is not particularly limited. Generally, any metal salts contained in metallic soap, preferably a sodium salt, can be used.

Specifically, examples of the metal salt of a carboxylic acid which can be used in the present invention include sodium tridecanoate, sodium myristate, sodium pentadecanoate, sodium palmitate, sodium heptadecanoate and sodium stearate. In addition, sodium oleate can also be mentioned as a usable salt in the fourth to sixth aspects of the invention.

First, the first to third aspects of the invention are described.

According to the first to third aspects of the invention described above, in a suspension containing the metal salt of a carboxylic acid and the high-boiling-point hydrocarbon suspended in water, the low-boiling-point hydrocarbon is brought into contact with them, to solidify. The high-boiling-point hydrocarbons in the first to third aspects of the invention are solid or liquid having a relatively not so large vapor pressure (that is, those not easily evaporated) at ordinary temperature and having preferably a boiling point of 60° C. or more. Preferably, they are saturated or unsaturated aliphatic hydrocarbon compounds (which may be either straight-chain or branched) containing 6 to 18 carbon atoms, or aromatic hydrocarbon compounds containing 6 to 9 carbon atoms. Specific examples include n-hexane, n-heptane, n-decane, 2,2,4-trimethylpentane, 1-decene, benzene, toluene, xylene, ethylbenzene and cumene.

Generally, the high-boiling-point hydrocarbon forms an aggregate substance more easily as the number of carbon atoms therein is decreased. However, in consideration of the easiness of separating the organic compounds from each other in the form of the formed aggregate substance of the high-boiling-point hydrocarbon and the low-boiling-point hydrocarbon to the original pure hydrocarbons, the high-boiling-point hydrocarbon having a larger number of carbon atoms can be more easily separated. Accordingly, a practically suitable combination is used by selecting, e.g. high-boiling-point hydrocarbons which are different in boiling temperature by 60° C. or more from low-boiling-point hydrocarbons to be solidified.

The low-boiling-point hydrocarbons that are solidified in the first to third aspects of the invention and that are capable of regeneration from the solidified product are organic compounds preferably having a boiling point of 40° C. or less, which are gaseous at ordinary temperature, or liquid that is evaporated easily due to their high vapor pressure (highly volatile liquid) at ordinary temperature. These are saturated or unsaturated aliphatic hydrocarbon compounds containing preferably 2 to 5 carbon atoms, more preferably 3 to 5 carbon atoms, which may be straight-chain or branched. For example, when a metal salt of pentadecanoic acid is used, all hydrocarbons containing 3 or 4 carbon atoms, and hydrocarbons containing 5 carbon atoms that are liquid at room temperature but evaporated easily due to their extremely high vapor pressure, can be solidified, and then regenerated from their solidified product.

Specifically, example of the low-boiling-point hydrocarbons which can be used in the first to third aspects of the invention include propane, n-butane, isobutane, n-pentane, branched pentane, ethylene, acetylene, propylene and butenes. These can be treated alone or in combination of two or more in a mixed system, but a distinct feature of this invention is that these are treated alone and can be taken out alone in a pure state, according to necessity.

In the first aspect of the invention, a suspension prepared by suspending the high-boiling-point hydrocarbon and the metal salt of a carboxylic acid in water is used. In this suspension, the low-boiling hydrocarbon is further brought into contact with them, thereby the low-boiling hydrocarbon is easily incorporated into the resultant aggregate substance, and the macroscopic aggregate substance can be formed under conditions near to those for the high-boiling hydrocarbon. Depending on the type of the low-boiling hydrocarbons, they can be solidified by leaving them at room temperature in a short period of time. This can be considered that hydrocarbon chains of the high-boiling-point hydrocarbon are first fixed via van der Waals force to alkyl chains of the metal salt of a carboxylic acid, and the low-boiling-point hydrocarbon is then fixed to these alkyl chains of the high-boiling-point hydrocarbon, to form an aggregate substance. This aggregate substance is formed in water, but upon formation, it is separated completely from water, and thus water is not contained in the aggregate substance.

Embodiments for formation of the macroscopic aggregate substance according to the method of the first aspect of the invention are not particularly limited. For example, there are:

(1) A method of adding the hydrocarbon high in boiling point under stirring, to an aqueous solution containing the metal salt of a carboxylic acid dispersed therein, followed by adding the desired low-boiling-point hydrocarbon thereto;

(2) A method of simultaneously stirring the metal salt of a carboxylic acid, the high-boiling-point hydrocarbon and water, followed by adding the desired low-boiling-point hydrocarbon thereto; and (3) A method of simultaneously stirring and mixing the four components, that is, the high-boiling-point hydrocarbon, the low-boiling-point hydrocarbon, the metal salt of a carboxylic acid, and water.

For example, the formation of a solid aggregate substance of hydrocarbons according to the method of the first aspect of the invention is conducted by heating a system comprising the metal salt of a carboxylic acid, the high-boiling-point hydrocarbon and water, to dissolve the metal salt of a carboxylic acid completely, then mixing them uniformly, and blowing the low-boiling-point hydrocarbon in a gaseous state. Water used is preferably pure water. Stirring is conducted preferably until the metal salt of a carboxylic acid is uniformly dissolved, emulsified or suspended. Generally, after the completion of blowing the low-boiling-point hydrocarbon and leaving the mixture at room temperature, then immediately a macroscopic aggregate substance composed of the high-boiling-point hydrocarbon, the low-boiling-point hydrocarbon and the metal salt of a carboxylic acid is formed and separated completely from water. Depending on the metal salt of a carboxylic acid used and the type of high-boiling-point and low-boiling-point hydrocarbons to be solidified, their solidified product may be formed more reliably, by gradually cooling the mixture after being left and then keeping it at a temperature lower than room temperature, or by heating the mixture at about 80° C. or cooling it at about 0° C. during stirring.

In the solidification method in the first aspect of the invention, the molar ratio of the metal salt of a carboxylic acid/the high-boiling hydrocarbon is preferably 1/10 to 1/1000, more preferably 1/10 to 1/500, and the molar ratio of the metal salt of a carboxylic acid/water is preferably 1/50 to 1/50000, more preferably 1/100 to 1/5000.

The amount of low-boiling-point hydrocarbons added thereto is preferably 1/10 to 1/1000, more preferably 1/10 to 1/500, in terms of the molar ratio of the metal salt of carboxylic acid/low-boiling-point hydrocarbon.

In the manner as described above, the total amount of the metal salt of carboxylic acid and high-boiling-point hydrocarbon and of the low-boiling-point hydrocarbon allowed to be coexistent therewith in water can be practically formed into a solid macroscopic aggregate substance.

The formed macroscopic aggregate substance can be also separated from water, by a usual means such as filtration or centrifugation, or by picking the aggregate substance up from water. This solid aggregate substance after formed is very stable, and it can generally be stably maintained even if the aggregate substance formed by heating or keeping it at low temperature is returned to room temperature. For example, an aggregate substance of sodium pentadecanoate, the high-boiling-point hydrocarbons and the low-boiling-point hydrocarbons is very stable generally up to about 60° C.

Now, the fourth to sixth aspects of the invention are described.

The hydrocarbons that are solidified in the methods of the fourth to sixth aspects of the invention and that are capable of regeneration from their solidified product may be those that are gaseous at ordinary temperature. These materials are preferably saturated or unsaturated aliphatic hydrocarbons containing preferably 4 or less carbon atoms, more preferably 2 to 4 carbon atoms, which may be straight-chain or branched. For example, when sodium pentadecanoate is used, all saturated hydrocarbons containing 3 or 4 carbon atoms, and unsaturated hydrocarbons containing 2 to 4 carbon atoms (excluding ethylene), can be solidified, and from this solid product, the hydrocarbons in the original state can be regenerated.

Specifically, examples of the gaseous hydrocarbons which can be used in the methods of the fourth to sixth aspects of the invention include propane, n-butane, isobutane, acetylene, propylene and butenes. These can be treated alone or in combination of two or more in a mixed system, but a distinct feature of this invention is that these can be treated alone and taken out alone in a pure state, according to necessity.

In the fourth to sixth aspects of the invention, the method of dissolving, emulsifying or suspending hydrocarbons and a metal salt of carboxylic acid in water is not particularly limited. Feeding of gaseous hydrocarbons at ordinary temperature, into water containing a metal salt of carboxylic acid suspended therein, can be conducted in a usual manner. For example, mention is made of a method of introducing gaseous hydrocarbons under high pressure and a method of feeding liquefied hydrocarbons.

Examples of concrete embodiments for forming the macroscopic aggregate substance according to the fourth aspect of the invention include the followings:

(1) Gaseous hydrocarbons are introduced under high pressure (preferably 0.5 to 5 MPa) into a pressure-resistant vessel containing a metal salt of carboxylic acid and water, then the metal salt of carboxylic acid is completely dissolved by heating, and the mixture is sufficiently stirred and left at room temperature.

(2) A pressure-resistant vessel containing a metal salt of carboxylic acid and water is cooled (preferably at −20 to −85° C.), then gaseous hydrocarbons are introduced into the vessel and liquefied, the vessel is sealed and heated to dissolve the metal salt of carboxylic acid completely, and the mixture is sufficiently stirred and left at room temperature.

(3) Hydrocarbons liquefied by pressurization are introduced directly, into a pressure-resistant vessel containing a metal salt of carboxylic acid and water, then the vessel is sealed and heated to dissolve the metal salt of carboxylic acid completely, and the mixture is sufficiently stirred and left at room temperature.

Heating for dissolving the metal salt of carboxylic acid is conducted for about 5 to 30 minutes at 30 to 95° C. depending on the type of the metal salt of carboxylic acid. Water used is preferably pure water. Stirring is conducted preferably until the metal salt of carboxylic acid is uniformly dissolved, emulsified or suspended. Generally, after stirring is finished, the mixture is left at room temperature for several hours to 1 day, thereby a macroscopic aggregate substance comprising the gaseous hydrocarbons and the metal salt of carboxylic acid is formed and separated from water, to float on water.

Depending on the metal salt of carboxylic acid used and the type of hydrocarbons to be solidified, the solidified product may be formed more reliably, by At gradually cooling the mixture after being left and then keeping it at a temperature lower than room temperature, or by heating it with boiling water before stirring.

In the solidification method in the fourth aspect of the invention, the molar ratio of the metal salt of carboxylic acid/the gaseous hydrocarbon is preferably 1/10 to 1/1000, more preferably 1/10 to 1/200, and the molar ratio of the metal salt of carboxylic acid/water is preferably 1/50 to 1/50000, more preferably 1/100 to 1/2000.

In the manner as described above, an almost total amount, excluding a little amount of gaseous hydrocarbons remaining in an upper part of the vessel, of gaseous hydrocarbons allowed to be coexistent in water with the metal salt of carboxylic acid, can be practically formed into a solid macroscopic aggregate substance.

The formed macroscopic aggregate substance can also be separated from water, by a usual separation means such as filtration, or by removing water through a lower drainage hole in the vessel in a method of pushing water out by utilizing the gas pressure of gaseous hydrocarbons remaining in an upper part of the vessel. This solid aggregate substance after formed is stable, and it can generally be maintained stably in a closed vessel even if the aggregate substance formed by heating or by keeping it at a low temperature is returned to room temperature. The solid aggregate substance formed in the method of the present invention may be evaporated at ordinary temperature and ordinary pressure, in an opened state (i.e. not in a closed vessel). To prevent this evaporation, the solid aggregate substance is stored in a vessel which can be closed. It is not necessary that this closed vessel is a pressure-resistant vessel, and any ordinarily used closed vessels can be used without particular limitation. For example, an aggregate substance of sodium pentadecanoate and gaseous hydrocarbons is generally stable at 50° C. or less when maintained in a closed vessel.

A solid aggregate substance formed by the method in the first aspect of the invention, for example, an aggregate substance of sodium pentadecanoate and high-boiling-point and low-boiling-point hydrocarbons, is initiated to be decomposed generally at 65° C. or more and completely decomposed upon heating at 80° C. or more. The temperature at which the aggregate substance is completely decomposed is varied depending on the type of the metal salt of carboxylic acid and the hydrocarbons, but the macroscopic aggregate substance is liquefied upon heating generally at 70° C. or more, or in some cases at 50 to 80° C., thereby it is separated into two layer solutions consisting of the metal salt of carboxylic acid and the high-boiling-point hydrocarbon, respectively. During this separation, the low-boiling-point hydrocarbon is completely evaporated and separated so that by collecting this gas, the original low-boiling-point hydrocarbon can be obtained. On the other hand, the high-boiling-point hydrocarbon in the original state can also be regenerated and obtained by a usual means, e.g. using a difference in density to separate the solution into the high-boiling-point hydrocarbon and the metal salt of carboxylic acid.

If the solid aggregate substance formed by the method in the fourth aspect of the invention described above is placed in an opened state by opening the closed vessel, the aggregate substance is decomposed while boiling generally at 20 to 30° C. under ordinary pressure, and the hydrocarbons contained in the solid aggregate substance is completely gasified and separated so that by recovering this gas, the original gaseous hydrocarbons can be obtained.

In addition, the aggregate substance can also be decomposed by heating in a closed state. For example, an aggregate substance of sodium pentadecanoate and hydrocarbons is initiated to be decomposed generally at 50° C. or more and completely decomposed by heating at 70° C. or more. The temperature at which the aggregate substance is completely decomposed is varied depending on the type of the metal salt of carboxylic acid and hydrocarbons, but the macroscopic aggregate substance is decomposed by heating generally at 70° C. or more, or at 50 to 80° C. depending on the case, and the gaseous hydrocarbons are completely gasified and separated.

The separated and recovered metal salt of carboxylic acid can be repeatedly used.

In the present invention, the low-boiling-point hydrocarbons (including gaseous hydrocarbons) can be handled in a solid form as described above, during transportation, storage, etc.

In the second aspect of the invention wherein a solid aggregate substance of low-boiling-point hydrocarbons is handled, the solid aggregate substance is handled preferably by keeping it at room temperature or less. In addition, this solid aggregate substance is handled preferably by keeping it in a closed vessel. For use of low-boiling-point hydrocarbons by release from their solid aggregate substance, the aggregate substance is heated and decomposed as described above, and the gasified components are collected.

In the fifth aspect of the invention wherein a solid aggregate substance of gaseous hydrocarbons is handled, the solid aggregate substance is handled by keeping it in a closed vessel, preferably at room temperature or less. For use of gaseous hydrocarbons by release from their solid aggregate substance, the aggregate substance is placed in an opened state by opening the closed-state, or the aggregate substance is heated in the closed vessel, as described above, thereby the aggregate substance is decomposed, and the components thus gasified are collected.

According to the method of the present invention, a wide variety of gaseous hydrocarbons and highly volatile liquid hydrocarbons can be safely and easily solidified, by utilization of the intermolecular van der Waals force between the hydrocarbons and the metal salt of a carboxylic acid (and high-boiling-point hydrocarbons, if necessary), and they can thus be converted, without using any harmful reagent, into such a form as to be safely stored, transported, etc. According to the present invention, since gaseous hydrocarbons or highly volatile liquid hydrocarbons can be handled in the form of solid during storage, transportation, etc., accidents and environmental pollution, such as leakage and ignition of the organic compounds, can be effectively prevented and transportation costs etc. can also be reduced. Further, the original hydrocarbons can be easily obtained, by releasing their solidified product under atmospheric pressure at room temperature, or by heating it if necessary, as well as the metal salt of a carboxylic acid can also be repeatedly used. The method of this invention as described can also be practiced even in an industrial scale.

Hereinafter, the present invention is described in more detail by reference to the following examples, which however are not intended to limit the invention.

EXAMPLES

Example 1

$10^{-3}$ mole of sodium pentadecanoate, $2 \times 10^{-1}$ mole of n-heptane and 1 mole of pure water were weighed, then placed in a glass vessel, sealed, heated to 85° C., and stirred with a vortex mixer, to form a uniform emulsion. The emulsion was returned to room temperature, and $2 \times 10^{-2}$ mole of n-butane was blown into it and left at room temperature for 10 minutes, thereby a white macroscopic aggregate substance appeared while the liquid phase was composed exclusively of colorless and transparent pure water. It was filtered to give 22 g of a stable (white waxy) solid aggregate substance.

Figure 2:
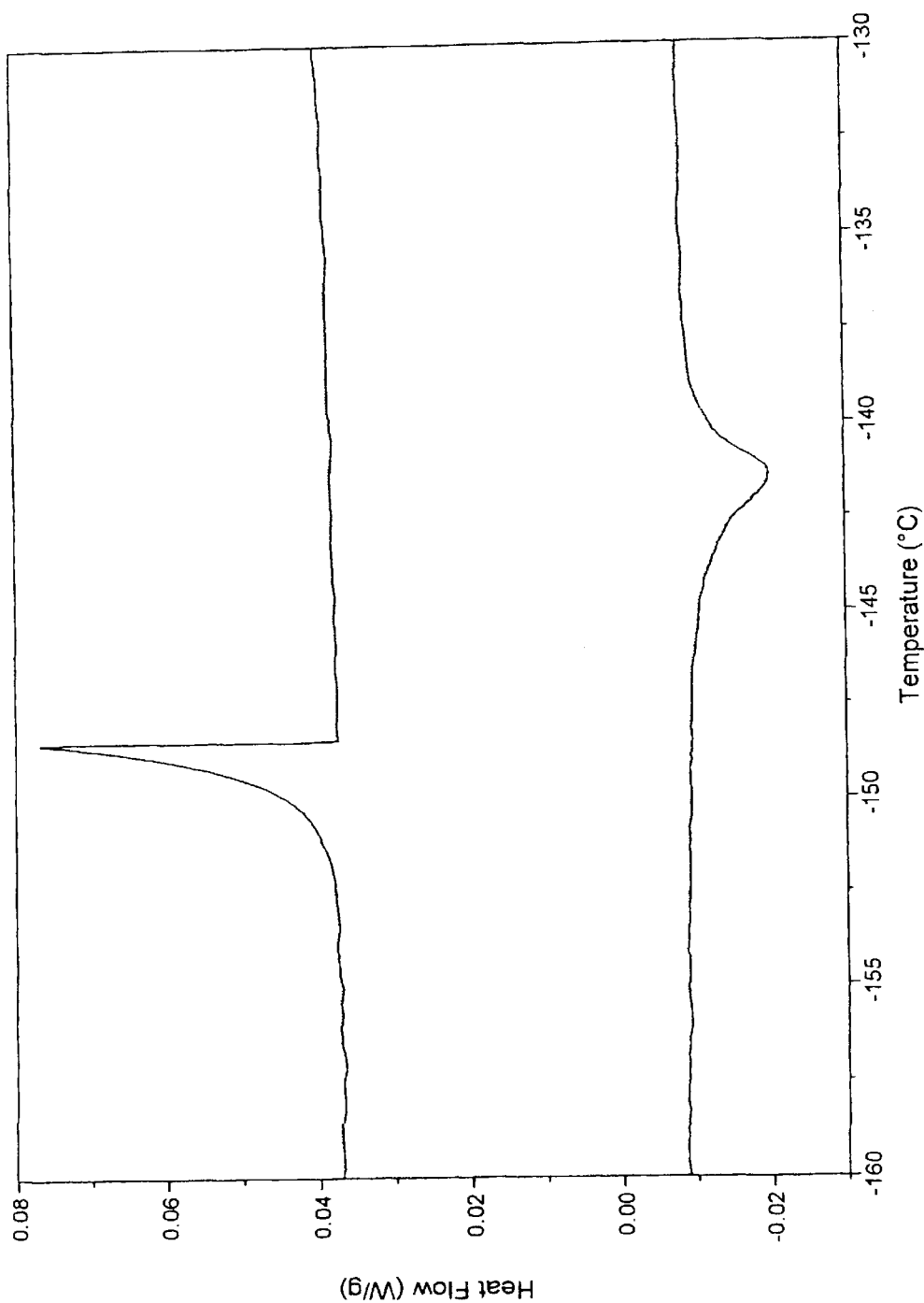
FIG. 2 is an enlarged view of a peak of n-butane in the graph of FIG. 1.

The result of this white waxy solid aggregate substance in differential scanning calorimetry (DSC) is shown in FIG. 1. In this graph, exothermal peaks in a cooling step (that is, at a decreasing temperature) are shown above (upper side) and endothermic peaks in a heating step (that is, at an increasing temperature) are shown below (lower side). The following peaks at decreasing and increasing temperatures show respectively the crystallization and melting of the following compounds: a major peak at −93° C. at both decreasing and increasing temperatures shows the crystallization and melting of n-heptane; a peak at −148° C. at a decreasing temperature and a peak at −144° C. at an increasing temperature, n-butane; a peak at −36° C. at a decreasing temperature and a peak at −0° C. at an increasing temperature, an aggregate substance of n-butane and sodium pentadecanoate; and a peak at about 55° C. at a decreasing temperature and complex peaks at 47° C. to about 70° C. at an increasing temperature, an aggregate substance of nheptane and sodium pentadecanoate. FIG. 2 shows an enlargement of a peak of n-butane in FIG. 1. As can be seen from the results in FIGS. 1 and 2, n-butane is maintained certainly in the white waxy solid aggregate substance.

Then, this aggregate substance was heated to 80° C. and gently shaken, thereby $10^{-3}$ mole of sodium pentadecanoate, $2 \times 10^{-1}$ mole of n-heptane (liquid) and $2 \times 10^{-2}$ mole of n-butane (gas) were obtained.

Example 2

The solidification procedure was carried out in the same manner as in Example 1, except that $2 \times 10^{-1}$ mole of ndecane was used in place of n-heptane, thereby, after being left for a whole day at room temperature, 31 g of a stable solid aggregate substance of n-decane and n-butane was obtained. This aggregate substance could be used to regenerate sodium pentadecanoate, n-decane (liquid) and n-butane (gas) by the similar heating decomposition and subsequent separation as in Example 1.

Example 3

The solidification procedure was carried out in the same manner as in Example 1, except that $2 \times 10^{-1}$ mole of 2,2,4-trimethylpentane was used in place of n-heptane, thereby 25 g of a stable solid aggregate substance of 2,2,4-trimethylpentane and n-butane was obtained. This aggregate substance could be used to regenerate sodium pentadecanoate, 2,2,4-trimethylpentane (liquid) and n-butane (gas) by the similar heating decomposition and subsequent separation as in Example 1.

Examples 4 to 6

The solidification procedure was carried out in the same manner as in Example 1, except that $2 \times 10^{-2}$ mol propane was used in place of n-butane, thereby 22 g of a stable solid aggregate substance of n-heptane and propane was obtained. This aggregate substance could be used to regenerate sodium pentadecanoate, n-heptane (liquid) and propane (gas) by the similar heating decomposition and subsequent separation as in Example 1. Using propylene or 1-butene, in place of propane, the same solidification and regeneration procedures as described above were conducted, thereby a stable solid aggregate substance was obtained in each case and it could be well used to regenerate the original materials by heating.

Examples 7 to 12

The solidification procedure was carried out in the same manner as in Example 1, except that sodium stearate was used in place of sodium pentadecanoate, thereby 22 g of a stable solid aggregate substance of n-heptane and n-butane was obtained. This aggregate substance could be used to regenerate sodium stearate, n-heptane (liquid) and n-butane (gas) by the similar heating decomposition and separation as in Example 1. Using sodium laurate, sodium tridecanoate, sodium myristate, sodium palmitate or sodium heptadecanoate, in place of sodium stearate, the same solidification and regeneration as described above were conducted, thereby a stable solid aggregate substance was obtained in each case and it could be used well for regeneration by heating.

Example 13

$2 \times 10^{-4}$ mole (52.8 mg) of sodium pentadecanoate and 0.2 mol (3.6 ml) of pure water were weighed, placed in a pressure-resistant glass vessel and cooled to −85° C. with dry ice/ethanol. n-Butane gas was introduced from a butane gas bomb via a thin tube into the pressure-resistant glass vessel. The butane was immediately liquefied. After $1.12 \times 10^{-2}$ mole (0.9 ml=650 mg) of the liquefied butane was introduced into the pressure resistant glass vessel, the vessel was closed, returned once to room temperature and heated to 72° C., and the sodium pentadecanoate was thus completely dissolved, vigorously shaken and stirred, thereby a uniform white suspension containing a large amount of white bubbles, consisting of sodium pentadecanoate, pure water and n-butane, was obtained. After left at room temperature, the solution in a lower part immediately became colorless and transparent, and after several hours, about 10 white particles with a diameter of 2 to 3 mm appeared in this colorless and transparent solution. The number of white particles was increased with the lapse of time to about 100, and the particles were mutually aggregated, to give, after several hours, 650 mg of a white, single and macroscopic self-aggregate substance composed of sodium pentadecanoate and n-butane, which was floating on the pure water.

This macroscopic self-aggregate substance was very stable in a closed system for a long period of time in the coexistence of water even at a room temperature of 30° C.

or more, but it was gradually decomposed at a temperature over 40° C. When released to atmospheric pressure, boiling of the self-aggregate substance was immediately initiated and it was completely decomposed.

When separated from water by declining the glass vessel, the macroscopic aggregate substance showed an increase in thermostability in a closed system and it could be stored stably for a long period of time at 50° C. or less. If the aggregate substance was kept at 50° C., its decomposition was initiated, but the decomposition immediately stopped in a closed system, and the majority of its white mass was kept stably as it was. More than half of the white mass was kept stably even at 60° C. At 70° C., it was completely decomposed, and sodium pentadecanoate dissolved in water as well as butane gas (partially liquefied in a closed system) was quantitatively obtained.

In this example, the composition after decomposition was 50 mg of sodium pentadecanoate and 600 mg of butane.

Example 14

$10^{-4}$ mole (23.6 mg) of sodium tridecanoate and 0.1 mole (1.8 ml) of pure water were weighed and placed in a pressure-resistant glass vessel, and 0.02 mole (1.9 ml) of liquefied butane was introduced into the pressure-resistant glass vessel in the same manner as in Example 1. The vessel was sealed, returned once to room temperature and heated to 60° C., and the sodium tridecanoate was thus completely dissolved, vigorously shaken and stirred, thereby a uniform white suspension consisting of sodium tridecanoate, pure water and n-butane was obtained. After left this overnight at room temperature, 1.3 g of a white self-aggregate substance composed exclusively of sodium tridecanoate and n-butane, floating on the pure water, was obtained.

Then, this aggregate substance was separated from the water, heated to 70° C. in a closed system and gently shaken, to give $10^{-4}$ mole of sodium tridecanoate and 0.018 mole of n-butane gas.

Examples 15 to 17

The solidification procedure was carried out in the same manner as in Example 14, except that $10^{-4}$ mole of sodium myristate, sodium palmitate, or sodium stearate was used in place of sodium tridecanoate, thereby 1.3 g of a stable solid aggregate substance of n-butane was obtained, respectively. Each of this aggregate substance could be used to regenerate n-butane gas by the similar decomposition by releasing or heating and subsequent separation as in Example 13 or 14.

Examples 18 to 20

The solidification procedure was carried out in the same manner as in Example 14, except that 0.02 mole of propylene, 1-butene or isobutane was used in place of n-butane, thereby 1 to 1.3 g of a stable solid aggregate substance was obtained, respectively. Each of this aggregate substance could be used to regenerate about 0.015 mole of gaseous propylene, 1-butene or isobutane by the similar decomposition by releasing or heating and subsequent separation as in Example 13 or 14.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A method of solidifying a gaseous hydrocarbon, comprising dissolving, emulsifying or suspending in water a metal salt of an aliphatic carboxylic acid and a hydrocarbon that is gaseous at ordinary temperature (20° C.), thereby forming a solid aggregate substance of the hydrocarbon.

2. The method of solidifying a gaseous hydrocarbon according to claim 1, wherein the molar ratio of the metal salt of an aliphatic carboxylic acid/the gaseous hydrocarbon is 1/10 to 1/1000, and the molar ratio of the metal salt of an aliphatic carboxylic acid/the water is 1/50 to 1/50000.

3. A method of regenerating a gaseous hydrocarbon, comprising heating the solid aggregate substance obtained by the solidification method in claim 1, to decompose said solid aggregate substance, thereby obtaining the gaseous hydrocarbon.

4. A method of handling a gaseous hydrocarbon, comprising storing or transporting the solid aggregate substance obtained by the solidification method in claim 1.

5. The method of handling a gaseous hydrocarbon according to claim 4, wherein the solid aggregate substance is handled with keeping in a closed vessel.

6. A method of regenerating a gaseous hydrocarbon comprising opening a closed vessel which comprises the solid aggregate substance obtained by the solidification method in claim 1, to decompose said solid aggregate substance, thereby obtaining the gaseous hydrocarbon.

7. The method of regenerating a gaseous hydrocarbon according to claim 6, wherein the solid aggregate substance is released under atmospheric pressure.

* * * * *